United States Patent [19]

Van de Velde

[11] Patent Number: 5,943,117
[45] Date of Patent: Aug. 24, 1999

[54] SCANNING LASER OPHTHALMOSCOPE FOR RETINAL MICROPHOTOCOAGULATION AND MEASUREMENT OF WAVEFRONT ABERRATIONS

[75] Inventor: Frans J. Van de Velde, Boston, Mass.

[73] Assignee: Jozef F. Van de Velde, Oosterzele, Belgium

[21] Appl. No.: 09/075,239

[22] Filed: May 9, 1998

Related U.S. Application Data

[63] Continuation-in-part of application No. 08/755,448, Nov. 22, 1996.
[51] Int. Cl.$^6$ ............................................. A61B 3/10
[52] U.S. Cl. .................................... 351/221; 351/205
[58] Field of Search ............................ 351/205, 210, 351/211, 221

[56] References Cited

U.S. PATENT DOCUMENTS 5,568,208  10/1996  Van de Velde ..................... 351/221

Primary Examiner—Huy Mai

[57] ABSTRACT

A combination of a confocal scanning laser ophthalmoscope and external laser sources is used for microphotocoagulation or the measurement of wavefront aberrations across the pupil of the eye. An opto-mechanical linkage device allows independent positioning of the pivot point of the Maxwellian view of the scanning laser ophthalmoscope and the pivot point of non-scanning external laser beams. The same pivot point is necessary to minimize wavefront aberrations and to enable precise focussing of a therapeutic laser beam on the retina. The pivot point of an external diagnostic laser beam is systematically moved across the anatomical pupil when wavefront aberrations of the eye optics are to be measured. The retinal location of the external laser beam is determined with two synchronized detectors and digital image processing techniques. One detector is used to localize moving fiducial landmarks of the retina. Independently, a second detector is used to locate the retinal backscatter caused by the external laser beam. This backscatter produces a convolved image with the retinal conjugate aperture and not a direct image of the external laser retinal location.

4 Claims, 5 Drawing Sheets

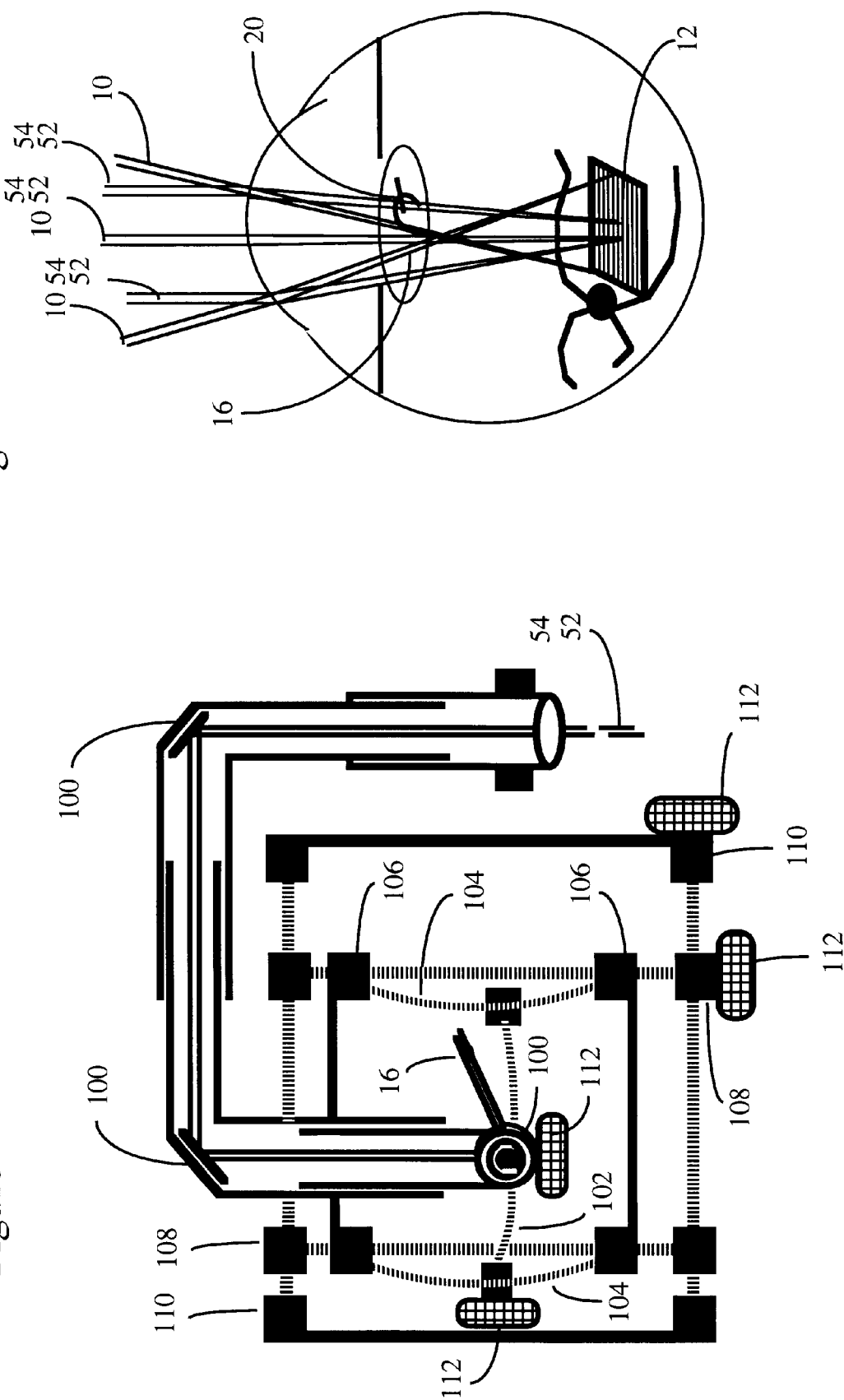

SCANNING LASER OPHTHALMOSCOPE FOR RETINAL MICROPHOTOCOAGULATION AND MEASUREMENT OF WAVEFRONT ABERRATIONS

CROSS REFERENCE TO RELATED APPLICATIONS

The invention is a continuation-in-part of U.S. patent application Ser. No. 08/755,448, filed Nov. 22, 1996, entitled "Scanning laser ophthalmoscope optimized for retinal microphotocoagulation" and is herein incorporated by reference. The invention is also related to U.S. Pat. No. 5,568,208, issued Oct. 22, 1996, entitled "Modified scanning laser ophthalmoscope for psychophysical applications" and U.S. patent application Ser. No. 9/033,900, filed Mar. 1, 1989, entitled "Maxwellian view and modulation control options in the scanning laser ophthalmoscope", both herein incorporated by reference.

BACKGROUND

1. Field of Invention

This invention relates generally to instruments for examining and treating the eye and specifically to a scanning laser ophthalmoscope with external laser sources for the purpose of retinal photocoagulation or the measurement of wavefront aberrations of the eye optics.

2. Description of Prior Art

The ophthalmoscope is well known as an important device for examining the eye, and in particular the retina. As a result of great interest in preserving eyesight, ophthalmoscopes of various constructions have been built. The latest version of the ophthalmoscope, a scanning laser ophthalmoscope, is particularly appealing because of its unique capability of combining the infra-red and angiographical imaging of the retina with psychophysical procedures such as the study of visual fixation, visual acuity measurements, and microperimetry. Only with the scanning laser ophthalmoscope, a unique, precise correlation between retinal anatomy and function can be established. This retinal function mapping is now known to be very helpful to the surgeon when delivering therapeutic laser applications to the retina. Until now however, these therapeutic laser applications have been delivered to the retina with an instrument other than the scanning laser ophthalmoscope. The use of different instruments renders the comparison of images and the interpretation of psychophysical testing more difficult.

U.S. Pat. No. 4,213,678, issued Sep. 29, 1980 to Pomerantzeff et al, discloses a co-pupillary scanning laser ophthalmoscope for the purpose of diagnosing and treating retinal disease using two different intensity levels of the scanning laser beam. One intensity range can be used for monochromatic imaging and angiography while a much higher level of the same laser beam or a different colinear scanning laser beam is used for retinal photocoagulation. This novel approach however is not ideal because of the technical difficulties in implementing safety controls for such scanning therapeutic laser beam, the difficulty in modulating the scanning laser beam over a range from non-coagulating to coagulating energies at video bandwiths, and the non-thermal complications of high intensity pulsed laser beams in the nanosecond domain.

In the prior art, an ophthalmoscope, for example the slitlamp or biomicroscope, is optically combined with a non-scanning therapeutic laser source for the purpose of retinal photocoagulation. In this modality, a contactglass is usually placed on the cornea to be able to view the retina with the instrument, and a mirror is used for reflecting the therapeutic laser beam onto the desired retinal location through a small part of the pupillary area. Importantly, the retina is illuminated and observed through different parts of the pupillary area to avoid reflexes, i.e. Gullstrand's principle of ophthalmoscopy. This optical arrangement makes the art of precise focussing of a small therapeutic laser beam on specific retinal levels more difficult in the presence of wavefront aberrations.

Furthermore, photocoagulating ophthalmoscopes have also been limited when such consistent small and localized laser applications in the retina are desired because the anatomical changes are difficult if not impossible to visualize during treatment in the presence of photocoagulating light. The critical endpoint of the laser application is therefore often exceeded. The surgeon, upon recognizing the minimal anatomical changes on the retina, is handicapped by a substantial human reaction time delay before he can interrupt the therapeutic laser. During this delay the laser continues to deliver energy to the retina and changes in the subject's fixation occur. Since the reaction time of the surgeon may exceed 200 ms, a 100 ms laser application can easily be wrongly targeted on the retina in the case of misalignment.

Also, it is difficult to avoid re-application of therapeutic laser to the same location or too close to another laser application because no reference to previous applications is available on the retinal image and the applications themselves are usually not visible some time after the initial treatment.

OBJECT, SUMMARY AND ADVANTAGES OF THE INVENTION

The principal object of this invention is to combine in one instrument the capabilities of imaging, psychophysics, and non-contact microphotocoagulation with optimal positioning and focussing of small therapeutic laser applications. This is accomplished by selecting an entrance location of the external therapeutic laser beam that is subject to minimal wavefront aberrations while observing the retina with the scanning laser ophthalmoscope using the same entrance location. Conversely, a second object of the invention is to measure the wavefront aberrations of the eye optics across the extent of the anatomical pupil by measuring the psychophysical or imaging properties of various entrance locations of an external diagnostic laser beam.

In essence, the invention is implemented by using: (1) A coupling system between the scanning laser ophthalmoscope and external laser sources comprising of a beansplitter and dedicated opto-mechanical linkage device. This linkage device allows the adjustment of position of the pivot point for the fast scanning diagnostic laser beams of the scanning laser ophthalmoscope relative to the pivot point of non-scanning external therapeutic or diagnostic laser beams. Optimizing the Maxwellian viewing of a retinal location will then also result in a minimal wavefront aberration for the external laser beams if the same pivot point is used. Also in this situation, the amount of prefocussing necessary to image on a specific retinal layer is a reference, if needed, for focussing a therapeutic laser beam with its proper telescopic optics. This telescopic optics can take into account dispersion of light caused by differences in wavelength. A wide entrance therapeutic Gaussian beam can produce diffraction limited applications of less than $50\mu$ in diameter. The concurrent small depth of focus or Rayleigh zone, allows focussing on specific levels. Smaller applications can also take into account spatial variations in the distribution of absorbing pigment. Fiber optic multimode transmission has the potential benefit of a flat beam profile but produces larger applications due to the well-known M-factor. It is important to realize that the reflection image of the application on the monitor cannot be used to determine or adjust focussing, hence the importance of a common pivot point.

(2) At least two detectors are genlocked in the confocal scanning laser ophthalmoscope. Using an appropriate beamsplitter and filters, one detector images the retina, its pigment distribution and the anatomical changes caused by the therapeutic laser, unimpeded by the therapeutic laser light. A second synchronized detector images only the reflected light from the external laser beam, without a background of moving retinal details. This image is actually an image of the confocal aperture and it can be localized in real-time using a computer with overlay framegrabber graphics cards capable of image processing techniques such as look-up table switching and two-dimensional normalized gray-scale correlation. The same algorithms can also find reference fiducial landmarks in the retinal image faster than human reaction time would allow.

In summary, the above means combine to enable the accurate placement of small, brief and localized therapeutic laser applications in specific layers of the retina, hence the term microphotocoagulation. With the proper selection of wavelength and therapeutic laser pulse characteristics, selective targeting of the photoreceptor layer and/or retinal pigment epithelium layer can be further improved. This removal of existing retinal pigment epithelium cells can be a first step in transplantation of genetically altered cells. Microphotoagulation has the ability to remove temporarily or permanently a percentage of the metabolically very active photoreceptors and/or retinal pigment epithelium cells, while minimizing damage to other anatomical structures, especially the nourishing choriocapillary layer and Bruch's membrane. Virtual "oxygen windows" are established. This approach is useful in the treatment or prevention of drusen related and neovascular age-related maculopathy. The retinal location, focussing, size, intensity and duration of therapeutic laser applications can be automatically stored and used for future reference. Dye-enhanced microphotocoagulation can assist in coagulating more efficiently the deeper vascular abnormalities in the retina, or subretinal dye injections can be used to permanently and selectively destroy photoreceptors.

If a diagnostic external laser source is used, the same invention can also calculate the wavefront aberrations of the complete eye optics by systematically varying the entrance location across the anatomical pupil in a parallel fashion. The differences in retinal location of the diagnostic laser beam and a reference location in the scanning laser raster are either measured or neutralized with small angulations of the external diagnostic laser beam. Zernike polynomial analysis can then reconstruct the wavefront aberrations from this data. Precise knowledge of the extended wavefront aberrations is for example useful in refractive surgery and photoreceptors may be oriented to the area of least aberrations.

Further objects and advantages of the invention will become apparent from a consideration of the drawings and ensuing description of a preferred embodiment.

DESCRIPTION OF THE DRAWINGS

FIG. 2 details the opto-mechanical linkage device coupling external laser sources and confocal scanning laser ophthalmoscope. Angulation and parallel movements of the laser beam are possible with the help of stepping motors under CPU control. The pivot points can be adjusted relative to each other.

FIG. 3 details the ray tracing of the scanning laser ophthalmoscope and external diagnostic or therapeutic laserbeams. A common pivot point is used to avoid lens changes in this example, thereby resulting in minimal wavefront aberrations and calculable focussing of the therapeutic beam location in the retina.

REFERENCE NUMERALS IN DRAWINGS

Figure 1:
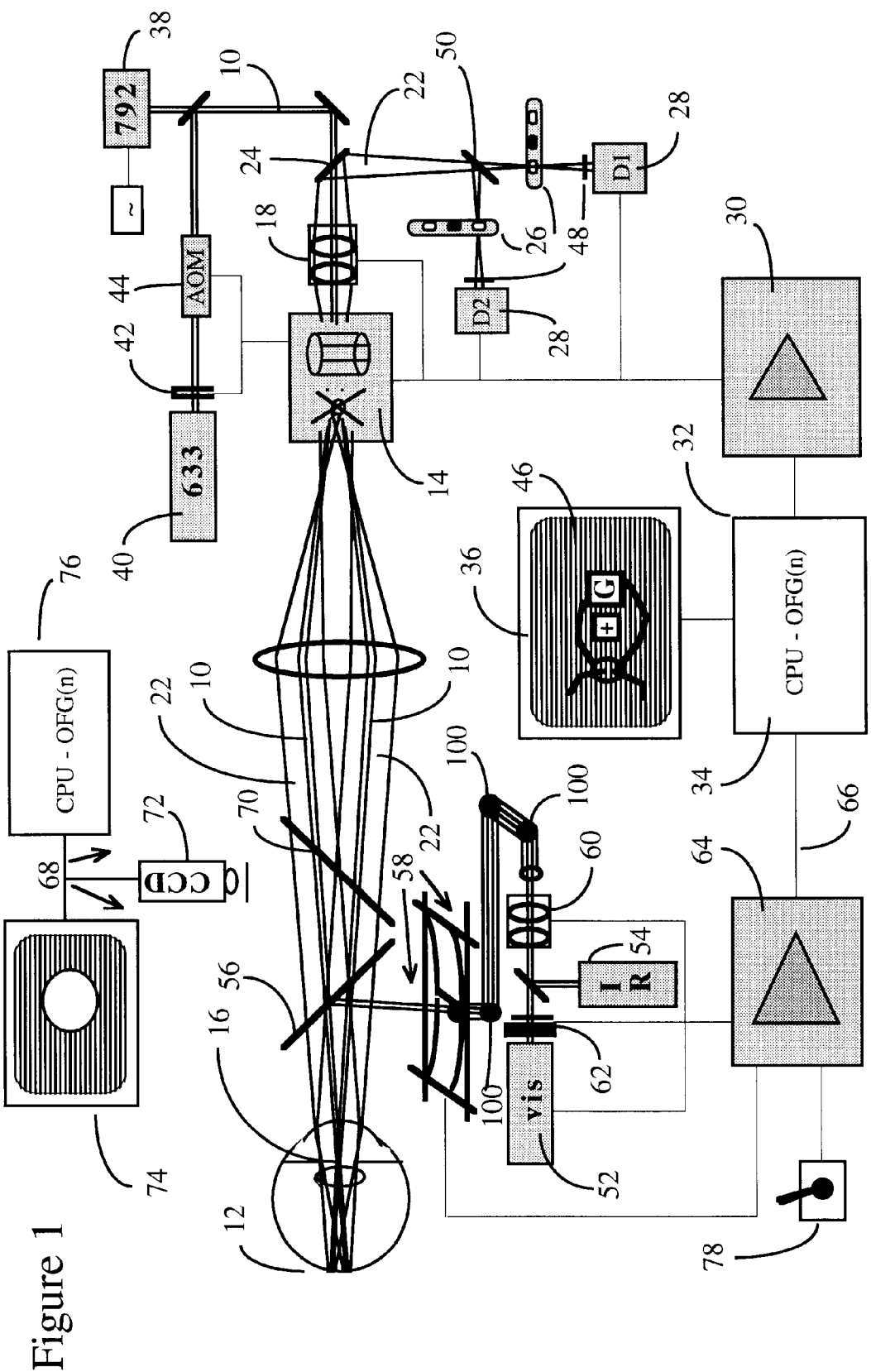
FIG. 1 is a diagrammatic representation, illustrating the different components of the confocal scanning laser ophthalmoscope for microphotocoagulation or measurement of wavefront aberrations. Five subparts can be distinguished. (1) A confocal scanning laser ophthalmoscope with lasers having visible and infra-red wavelengths, synchronized detectors, beamsplitter, confocal apertures and filters, collimator-telescope prefocussing optics, scanning optics, synch and video-generating electronics, acoustooptic modulator (AOM). (2) External diagnostic or therapeutic non-scanning lasers with modulation device, coupled to the scanning laser ophthalmoscope with the help of a beamsplitter and opto-mechanical linkage device, safety shutter, collimator-telescope, and control electronics. (3) The computer with overlay framegrabber graphic card(s) capable of digital image processing, and monitor. (4) An optional Maxwellian view control comprising a beamsplitter and CCD camera.

10 Gaussian beam of laser light
12 Posterior pole of the eye
14 Scanning optics, including polygon and galvanometer 16 Maxwellian view illumination of diagnostic and therapeutic beams, pivot point
18 Collimator-telescope for scanning laser beams of ophthalmoscope
20 Lens changes, scattering elements in the eye
22 Backscattered light returning from the retina
24 Beamsplitter-separator for incident and backscattered laser light
26 Aperture located at a conjugate plane of the waist of scanning laser beams
28 Avalanche photodiodes, genlocked
30 Video-generating and synchronizing electronics of scanning laser ophthalmoscope
32 Master timing signal generator
34 Computer with overlay frame grabber graphic card(s) and frame memory
36 video display monitor
38 Diagnostic scanning diode infra-red 792 nm laser
40 Diagnostic scanning He—Ne 633 nm laser
42 Pair of adjustable linear polarizers
44 Acousto-optic modulator
46 Overlay graphics on retinal image, indicating location of external laser spot
48 Barrier filter, optionally with pinhole at pupillary conjugate plane
50 Beamsplitter for separating scanning and external laser beams
52 External, non-scanning therapeutic or diagnostic laser source
54 Second infrared or visible wavelength external laser source
56 Beamsplitter combining light from scanning and external laser sources
58 Opto-mechanical linkage device
60 Collimator-telescope for external laser beams
62 Safety shutter, acousto-optic modulator
64 Electronic circuitry for elements 52, 54, 58, 60, 62
66 I/O link between circuitry 64 and computer
68 Means for determining location of pivot point in anterior segment of eye
70 Beamsplitter
72 CCD camera
74 Monitor
76 Computer, graphics adaptor
78 Joystick-micromanipulator, optional bite-bar
100 Adjustable mirror hinges
102 Support arc with lead screw for positioning element 100
104 Pair of support arcs with leadscrew for positioning element 102
106 Supporting framework for elements 100, 102 and 104
108 Adjustable leadscrew support for positioning element 106
110 Framework with adjustable lead screw to position element 108
112 Stepping motors to position the elements 100, 104, 106, 108
150 Dioptric media of the eye, eye optics
152 Cornea
154 Lens
156 Anterior chamber fluid
158 Vitreum
160 Retina
162 Photoreceptor layer
164 Nerve fiber layer
166 Choriocapillary layer
168 Retinal pigment epithelium layer
170 Bruch's membrane layer
172 Virtual retinal conjugate aperture with waist of scanning laser beams
174 Reflection, backscatter from non-scanning external laser source, beam
176 Wide, 2 mm highly collimated entrance beam of scanning laser (Gaussian)
178 Narrow, 1 mm collimated entrance beam of scanning laser

DETAILED DESCRIPTION AND OPERATION OF AN EMBODIMENT

A typical embodiment of the confocal scanning laser ophthalmoscope for retinal microphotocoagulation or the measurement of wavefront aberrations is illustrated in FIG. 1. The principles of scanning laser ophthalmoscopy are described in detail in the prior art. Features of the confocal scanning laser ophthalmoscope that are relevant to the invention are further discussed.

I. THE CONFOCAL SCANNING LASER RETINOSCOPE

A prefocussed Gaussian beam of laser light 10, e.g. 1.0 mm in diameter, is further focussed by the eye optics of approximately 60 D power, to a spot, typically between 10 and $30\mu$ in diameter at a retinal plane, and this spot is scanned over the posterior pole of the eye 12 in a sawtooth manner with the help of scanning optics, currently a polygon and galvanometer driven mirror 14. Fast horizontal 15 KHz and slower vertical 60 Hz deflections of this flying laser spot correspond to a standard video RS-170 rate and create the rectangular laser beam raster on the retina. A rectangular area of about 0.5 cm$^2$ on the retina is illuminated in the 40 degree field of view of the instrument. A Maxwellian view illumination is used in the scanning laser ophthalmoscope. The pivot point 16 of the scanning laser beam is well-defined and is optimally positioned, e.g. in the plane of the anatomical pupil, in order to minimize the effect of wavefront aberrations on the retinal image. The amount of prefocussing is adjusted with a collimator-telescope 18 and results in the positioning of the waist of the Gaussian beam at specific planes in the retina. The field of view can he changed from 40 degrees to 20 degrees. In the 20 degree field of view, the pivot point 16 of the Maxwellian view is wider in diameter as the Gaussian beam is doubled in diameter. Because of the wider beam in the 20 degree field of view, it will be more difficult to minimize wavefront aberrations by moving the pivot point around focal scattering or absorbing elements in the ocular media 20.

In the confocal scanning laser ophthalmoscope, the light that returns from the retina 22, now distributed in the anatomical pupil, is descanned over the same optics, separated from the illuminating beam at mirror-pinhole 24, and usually passed through a small aperture 26. This aperture, e.g. 1 mm in diameter, is conjugate with a virtual aperture of e.g. $100\mu$ at the retinal beam waist. It is used to reduce backscattered light outside the illuminated area on the retina. The amount of light that falls on an avalanche photodetector 28 is translated into an analog signal by the video and synchronization generating circuitry 30 of the scanning laser ophthalmoscope. This signal is synchronized to the master timing signal provided by the rotating polygon. The video signal is then relayed to the overlay frame grabber graphics cards 32 within the computer 34, which in turn will display the processed signal onto a display monitor 36.

Often two laser sources are aligned to illuminate the retina. The two lasers serve a different purpose. A high intensity diode infra-red 780 nm laser 38, under electrical modulation control and vertically polarized, is nearly invisible to the observer. It produces the retinal image on the display monitor 36. An aligned and low intensity He—Ne 632.8 nm laser 40, horizontally polarized, is modulated with a pair of linear polarizers 42 and acousto-optic modulator 44. The 633 cm laser 40 is used to draw visible graphics in the laser raster. These visible graphics are created by amplitude modulation of the laser 40. For this purpose, the acousto-optic modulator 44 is usually driven by the same computer overlay frame grabber graphics card 32. The graphics, which are seen by the observer, are usually not visible in the retinal image, unless when they area very bright. The exact position and characteristics of the graphics can however be indicated in real-time on the retinal image with the help of computer generated overlays 46 because the image video that comes out of the scanning laser ophthalmoscope and graphics video that modulates the acousto-optic modulator 44 are synchronized to the same timing signals provided by the synchronization generating circuitry 30. The 632 nm He—Ne laser 40, typically used for generating the graphical stimuli at lower intensities, could however also be used for imaging at higher intensity levels.

Multiple and synchronized detectors 28 and multiple laser sources 38,40 have been used before in the original red-yellow krypton color co-pupillary scanning laser ophthalmoscope. Appropriate barrier filters 48, and beamsplitter 50 are necessary in this situation, matching the different wavelengths that are used.

Surface-emitting quantum-well laser diodes are of increasing interest, and offer the advantages of high packing densities on a wafer scale. An array of up to a million tiny individually modulated cylindrical $In_{0.2}Ga_{0.8}As$ surface-emitting quantum-well laser diodes, VCLES, with lasing wavelengths in the vicinity of 970 nm and shorter can substitute the traditional laser sources 38, 40 and scanners 14 if coupled with a two-dimensional detection array. The use of such a specific extended detection array has been discussed in the original U.S. Pat. No. 4,213,678.

An additional combination of an aperture with filter 48 can be positioned after descanning the returning light in the neighborhood of a pupillary conjugate plane, for example in front of the photodetector 28. If small apertures are used here, the exit pupil of the returning light will be restricted. The backscattered light having the direction of the illuminating laser is then favored. This property is used in combination with a small aperture 26 for reflectometric measurements. Applications can be found in the field of Stiles-Crawford, photopigment and wavefront aberration measurements.

II. DIFFERENT EXTERNAL LASER SOURCES AND THEIR CONTROLLING MEANS

External therapeutic laser sources 52, 54 are well known in the prior art, e.g. argon or currently diode laser 52, having the possibility of emitting different wavelengths, for example 488 nm, 514 nm, 532 nm and 840 nm. A variable part of the optical transmission can occur over fiber-optics. Smaller spot sizes can be obtained on the retina however when only mirrors and lenses are used in combination with a fundamental mode laser. The advantage of fiber optics is flexibility and a flat intensity profile at the exit aperture. Multimode transmission, including fiber optics transmission, is more difficult to focus to a small spot size due to the M-factor.

The external therapeutic lasers can be pulsed, for example with the help of an acoustooptic modulator 62, to selectively target absorbing layers, for example the pigment epithelium 168. Therapeutic lasers can be used in association with absorbing dyes. In photodynamic therapy, a photosensitizing drug is first injected and laser is then applied with the aim of closing off small bloodvessels. In a second stage, classic argon photocoagulation can penetrate more completely in deeper layers because the blood flow has been halted before with this photodynamic therapy and stationary hemoglobins are far more effective in absorbing energy, together with the melanin pigment. Another dye, e.g. fluorescein, can be injected between the photoreceptors 162 and pigment epithelium 168, thereby causing localized small artificial serous retinal detachments. Delivery of short duration 488 nm applications can then selectively destroy photoreceptors 162 at the dye-photoreceptor interface without destruction of the deeper or more superficial layers 164, 168, 170, 166. Often, an aligned low power therapeutic beam 54 is provided for aiming purposes. Alternatively, the high power therapeutic laser beam 52 can also serve as an aiming beam at much lower intensities.

External diagnostic and non-scanning laser sources 52, 54 include He—Ne red, He—Ne green, and optimized, collimated diodes. They are used for the reconstruction of wavefront aberrations across the anatomical pupil of the eye. Clean and small beam profiles are important here. External diagnostic lasers 52, 54 differ from the therapeutic sources in the maximum power output they can produce. Otherwise, a similar transmission system is used, preferably avoiding fiber-optics. Surface-emitting quantum-well laser diodes are of increasing interest, and offer the advantages of high packing densities on a wafer scale. An array of individually modulated cylindrical $In_{0.2}Ga_{0.8}As$ surface-emitting quantum-well laser diodes, VCLES, with lasing wavelengths in the vicinity of 970 nm and shorter can substitute the external diagnostic laser sources 52, 54 and their translational movement as described in a later section. A collimator-telescope adjusts the spacing and alignment of the individual laser beams from the VCLES.

Essential in the optical pathway is a collimator-telescope 60 for precisely selecting the spot size and focussing of the external laser beams 52, 54 on a specific retinal plane. The amount of focussing that is needed for the external laser beams 52 and 54, is related to the amount of prefocussing of the scanning lasers 38 and 40 for the same retinal area since the same optical pathway is used through the ocular media. This focussing can take into account the dispersion of light that is caused by differences in wavelength. Another important element in the optical pathway is a safety shutter, filter and/or modulating device 62 allowing specific pulsating patterns of energy to be delivered. The foregoing components are controlled by electronic circuitry 64, known in the prior art. In addition, an I/O link 66, often a combination of TTL circuits, exists between the control electronic circuitry 64 of the external lasers and the computer 34. This electronic connection 66 can signal to the computer 34 when the external lasers 52 and 54 are used and also allows activating the modulating means 62 under control of the computer 34.

III. THE OPTO-MECHANICAL LINKAGE DEVICE AND RAY TRACING

The external diagnostic or therapeutic laser beams 52, 54 are non-scanning, however their orientations, both rotational and translational, are allowed to change, using a special transmission system comprising a beamsplitter 56 and opto-mechanical linkage device 58. FIG. 2 illustrates the essential opto-mechanical linkage device 58 between the external therapeutic or diagnostic laser sources 52, 54 and the confocal scanning laser ophthalmoscope for the purpose of microphotocoagulation or the reconstruction of wavefront aberrations. Also, the methods are described by which (1) the position of the external laser beams 52, 54 are referenced on the retinal image, (2) a precise focussing is possible for the purpose of microphotocoagulation, and (3) wavefront aberrations can be reconstructed.

The part of the opto-mechanical linkage device 58 that transmits the external laserbeams is preferably realized with a combination of extendable mirror hinges 100, but can use flexible fiber optics instead. Mirror optics permit better focussing to a smaller waist when a Gaussian beam of larger entrance beam diameter is used. Enough degrees of freedom are available with the mirror hinges 100 as to permit unimpeded movement of the laserbeams in a rotational and translational fashion.

The opto-mechanical linkage device 58 consist further of a framework or base 106 that permits a support arc 102 to slide across using another pair of support arcs with lead screw 104. The last mirror hinge 100 or terminal part of the fiber-optic can contain additional optical elements and is attached to the support arc 102. This terminal part of the transmission optics can slide along the support arc 102 and reflects the therapeutic laser light 52, 54 coming from the other components in the opto-mechanical linkage device 58 towards the posterior pole of the eye 12. The two sliding movements allow the external laser beams 52, 54 to move perpendicular to a curved surface, e.g. a part of a sphere, such that the external laser beams 52, 54 will have a pivot point 16 that is very similar in location to the pivot point 16 of the Maxwellian view of the scanning laser ophthalmoscope. The two sliding movements can be produced with the help of stepper motors 112, but several other means and methods can be easily envisaged to perform this function, either manually or motorized. A micromanipulator-joystick 78 is used to control these stepper motors. The joy-stick 78 is moved by the surgeon to select a retinal location to treat. The joy-stick 78 is also moved by the observing subject to neutralize wavefront aberrations for different entrance location as explained below. The supporting framework 106 typically measures about 100 mm by 100 mm and is attached to the confocal scanning laser ophthalmoscope through the adjustable supporting elements with leadscrews 108 and 110. The elements 108 and 110 permit the framework 106 to move translationally in two directions with the help of stepper motors 112. These translational movements can also be accomplished manually or through equivalent means and methods. Computer controlled translational movements will be used to measure wavefront aberrations as further explained.

The prefocussed external laser beam 52 usually has a 0.5 mm to 2 mm diameter at the entrance position in the eye. The external beams 52, 54 are prefocussed by the collimator-telescope 60 using as a reference the amount of prefocussing of the scanning laser beams 38, 40 for the same retinal location and using the same pivot point 16. The therapeutic beam 52 is then further focussed by the eye optics to a spot that can be as small as $10\mu$ on the retina if a wide Gaussian entrance beam and mirror optics are used. Focussing can take into account the effect of chromatic dispersion that has been tabulated in the prior art. As mentioned before, focussing will be more precise in the 20 degree field of view of the scanning laser ophthalmoscope.

Figure 6:
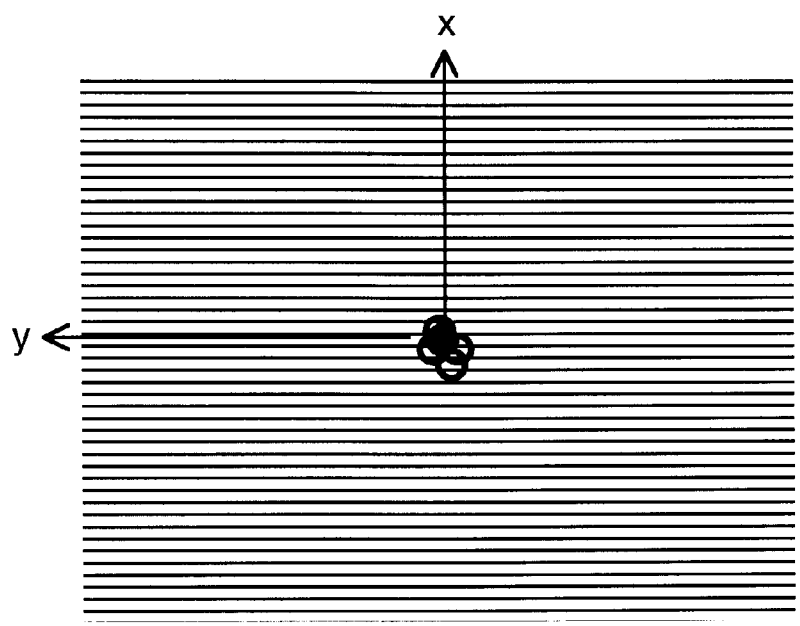
FIG. 6 details the contents of frame memory of an OFG card with video coming from second synchronized detector. The coordinates of the location of the external beam can be determined with simple digital image processing techniques and indicated on the retinal image with the help of overlay graphics.

It is important to understand the raytracing of both scanning and external laserbeams for the purpose of microphotocoagulation or the reconstruction of wavefront aberrations. FIG. 3 illustrates the different possibilities that can exist in an eye having some lens changes or scattering elements 20 in the dioptric media that cause wavefront aberrations. Such changes however can occur at the corneal level as well. In order to ensure that both the scanning lasers 38, 40 and external lasers 52, 54 are subject to similar wavefront aberrations, it is necessary that these beams use the same path and hence the same pivot point 16. This pivot point 16 can be chosen by the observer so that a particular retinal location is seen in good focus with minimal aberrations on the monitor 36. As a result, the therapeutic external laser beams 52, 54 will also undergo minimal aberrations and will be focusable using the telescope-collimator 60. If the pivot points 16 were different, aberrations could influence both the beamshaping and focussing of the therapeutic laser spot. This is very important since it is not possible to see directly the impact of the external laser beams 52, 54 on the retina as explained below. On the contrary, when reconstructing wavefront aberrations, the pivot point 16 for the external laser beams 52, 54 will be systematically moved, e.g. under control of a computer program, relative to the pivot point 16 of the scanning laser beams. These movements should only be translational in order to move the external diagnostic laserbeams 52, 54 in a parallel fashion. If no aberrations are present, parallel beams will focus on the same retinal location. In the presence of aberrations, the diagnostic external laser spot on the retina will be different by a various amount in quality and more important in location, for the different parallel entrance positions into the eye optics. Different retinal locations are illustrated in FIG. 6. These differences in location relative to a reference spot created by the fixation target in the scanning laser ophthalmoscope, can be recorded by the frame grabber and subsequently analyzed. It is possible to simplify the opto-mechanical linkage device if only wave-front aberrations are to be measured by the reflectometric method. In this case, only translational parallel movements of the diagnostic external laser source are necessary. Alternatively, the subject could slightly alter the orientation of the external diagnostic beam 52, 54 with the help of joystick-micromanipulator 78 as to neutralize the difference in location on the retina. The amount of angulation required is again measure of the degree of wavefront aberration corresponding to a particular entrance position of the external beam into the eye optics. The data coming from a grid of different entrance positions will be used to reconstruct the wavefront aberrations across the anatomical pupil of the eye using e.g. the well-known method of zernike polynomial analysis or equivalent algorithms.

Figure 7:
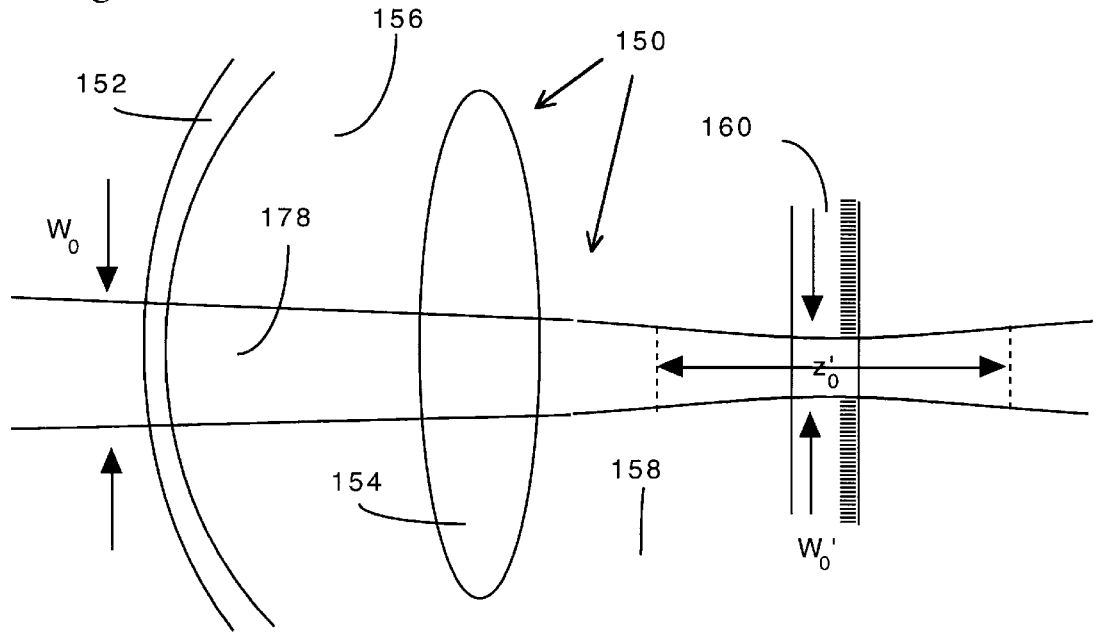
FIG. 7 is a schematic that illustrates a stationary raytracing through dioptric media of a Gaussian beam with a narrow entrance waist $W_0$. This results in a larger spot size on 0the retina $W_0'$ and a large depth of focus $z_0'$.
Figure 8:
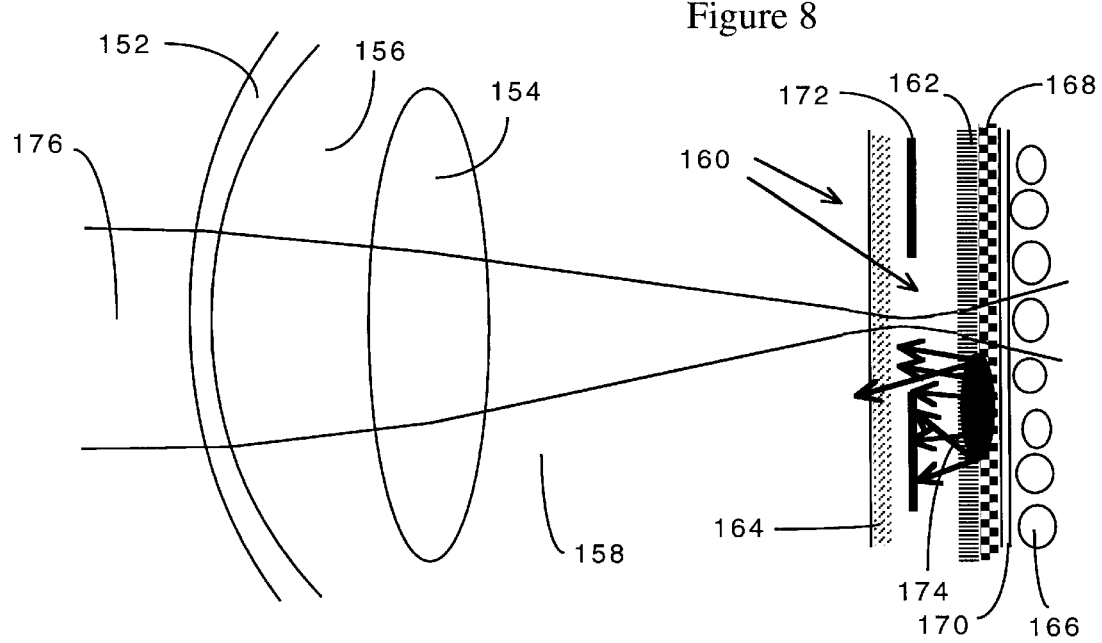
FIG. 8 illustrates a wider entrance beam through the eye optics of cornea and lens. The beam focusses to a smaller spot in the retina. Different retinal layers, virtual retinal conjugate aperture and reflection of non-scanning external laser source are indicated.

Gaussian beam optics are illustrated in FIG. 7 and FIG. 8. In FIG. 7, a fairly small diameter, less than 1.0 mm collimated entrance beam 178 is used. It can represent both a scanning laser beam 38, 40 or external laser beam 52, 54. It demonstrates the fact that beams of small waist diameter $W_0$ will focus into a relatively large spot $W'_0$, however with a large depth of focus or Rayleigh zone $z'_0$. A wider entrance beam, as illustrated in FIG. 8, is useful for creating small localized therapeutic applications in the retina. The smaller entrance beam of FIG. 7 is useful for the reconstruction of wavefront aberrations for two reasons. First, a small entrance beam can resolve many locations at the entrance pupil of the optical system and second, the spot will be more uniform is size and focus on the retina in the case of aberrations. This in turn is helpful in determining the location of the retinal spot.

Highly reflective beamsplitters 50, 56 for the wavelength and polarization of the external lasers 52, 54, but highly transparent for the wavelengths of the other scanning diagnostic lasers 38, 40 of the scanning laser ophthalmoscope, are optimally coated according to the principles outlined in the related U.S. Pat. No. 5,568,208. The task of the beamsplitter 56 is to direct the external laser beams 52, 54 and various scanning diagnostic laser beams 38, 40 of the scanning laser ophthalmoscope towards the posterior pole of the eye 12. The task of beamsplitter 50 is to direct the returning light from scanning lasers 38, 40 and external lasers 52, 54 to different detectors 28. Some therapeutic laser light 52, 54 is however permitted to pass the beamsplitter 56 in order to reach a photodetector 28 after returning from the retina. The remaining transmitted therapeutic light 52, 54 through the beamsplitter 50 is absorbed by filter 48, to avoid confusion with the descanned laser light 38 or 40 that is returning from the retina. As mentioned before, all detectors 28 are genlocked to a common master timing signal for producing video output. This property is used in referencing the external laser beam location onto the retina. For this purpose one detector 28 is provided with a barrier filter 48 to eliminate all wavelengths of light returning from the retina except the external laser wavelength. It is well known in the art of digital signal and image processing how to calculate the position of the returned patch of light from the external laser beams in the video-signal. Because of the synchronization of the video generated from the detectors 28 within the overlay frame grabber graphic card(s) memory 32, a precise indication of the position of the external laser beams 52, 54 is possible using overlays 46 on the retinal image. It is important to realize that this separation of laser beams at the detectors 28 is necessary for multiple reasons. First, it is easier to see the development of a retinal coagulation in the absence of the treating light.

Figure 5:
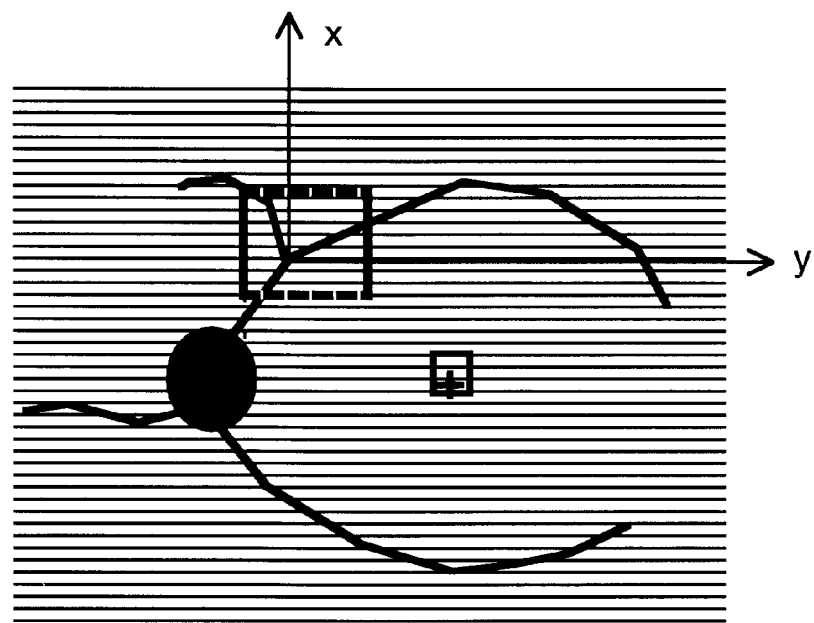
FIG. 5 details the contents of frame memory of an OFG card with video coming from one detector. A small search window within the video image contains a gray scale pattern that is used in normalized gray-scale correlation to determine the coordinates of fiducial landmarks of the retinal image.

Second, the overwhelming power of the external laser beams makes their precise localization on the retina impossible because of oversaturation of the video. Third, tracking algorithms as explained below cannot work efficiently in the presence of a retina that can move independently in a different direction when compared with the position on the retina of the external laser beam that can move in another direction. Very importantly, only the location but not the focussing and size of the external beam 52, 54 is determined by the above procedure This is so because the external laser beams 52, 54 will generate an image of the confocal aperture 26 on the monitor 36. This can be understood by examining FIG. 8. In this FIG. 8, the following thought experiment is realized. The scanning laser beam 176 is held stationary while traversing the dioptric media of the eye 152, 156, 154, 158. Further visualized are the virtual confocal aperture 172 at the waist of the laser beam 176 and the different parts of the retina, 164, 170, 162, 168, 166. An external laser beam 52, 54 produces the retinal spot 174. This retinal spot backscatters light, e.g. from the retinal pigment epithelium 168. In order to complete the thought experiment, the retina is moved instead of the stationary laser beam 176. This situation is now completely equivalent to a real scanning laser ophthalmoscope. An image of the opening of the confocal aperture 26, 172 will be generated on the monitor 36 by the passing external laser spot 174. FIG. 5 and FIG. 6 summarize what is seen by the two synchronized detectors 28. In FIG. 5 only the scanning lasers 38, 40, and most often only the scanning IR laser 38 responsible for the retinal image, is contributing. The graphics however can be seen as overlays 46 as previously explained. Diverse retinal features can be used as fiducial landmarks, e.g. the branching pattern of vessels or pigmentary changes. In FIG. 6 only the external lasers 52, 54 will contribute to the image. Different locations are represented that correspond to different entrance positions in the presence of aberrations of the dioptric media of the eye. As previously discussed, the spots actually represent the shape of the confocal aperture 26, 172 that is used and not the shape of the retinal spot.

Location, focussing, size, duration of application and intensity of the therapeutic laser beam can be stored, retrieved and used in other treatment sessions. It is also possible to plan laser applications at particular locations on forehand. Since the registration of the therapeutic laser beam location is happening in real-time, simultaneous retinal image registration using a technique outlined in the next chapter, will show whether the intended therapeutic laser beam location is still selected within the desired area on the retina. If a misalignment occurs, the TTL circuitry 66 will activate the shutter 62 and interrupt the therapeutic laser beam 52. This is very advantageous since such interruption is likely to occur much faster than human reaction would allow.

IV. MAXWELLIAN VIEW CONTROL OPTIONS

It is important to know the entrance position of the maxwellian view of a reference fixation target or retinal location produced by the scanning lasers 38, 40 and the entrance position of the external diagnostic lasers 52, 54 with regard to the anatomical pupil and anterior segment of the eye. This knowledge is necessary to reconstruct the wavefront aberrations of the eye because the anatomical pupil is a fiducial structure that is used to map these wavefront aberrations. With other words, each significant entrance position of the external diagnostic beam should be documented together with the entrance position of the scanning laser rays that correspond to a fiducial landmark on the retina. The test should be short enough to keep the latter entrance position constant by preventing lateral eye movements. A bite-bar or data correction may be necessary if the test duration is longer. Small rotations of the eye, because of fixation instability, will cause this reference fiducial landmark to shift. These shifts however are neutralized because the distance between such fiducial landmark and the retinal location of the external diagnostic laser beam rather than the absolute position of the external laser beam is taken into consideration for the purpose of calculating wavefront aberrations. The above consideration is important in the reflectometric method. In the psychophysical method, the subject will make a reference fixation target coincide with the spot of the moving external laser beam 52, 54 or angulate of this beam with the micromanipulator 78. Variations in fixation are averaged out by the subject and do not have to be taken into account. Means 68 and alternative methods to document, verify or change in a controlled manner the entrance locations of the Maxwellian view have been documented extensively in U.S. Pat. No. 5,568,208, issued Oct. 22, 1996, entitled "Modified scanning laser ophthalmoscope for psychophysical applications" and U.S. patent application No. 9/033,900, filed Mar. 1, 1989, entitled "Maxwellian view and modulation control options in the scanning laser ophthalmoscope", both herein incorporated by reference. Means 68 typically includes a beamsplitter 70, CCD camera 72, and equipment 74, 76 for analyzing the video illustrating the location of the Maxwellian view. In the absence of active control of the entrance location, a bite-bar would be necessary to maintain and document a specific entrance location. The Maxwellian view control is much less important for the purpose of microphotocoagulation and can be omitted in this case.

V. THE OVERLAY FRAMEGRABBER AND IMAGE PROCESSING TECHNIQUES

Figure 4:
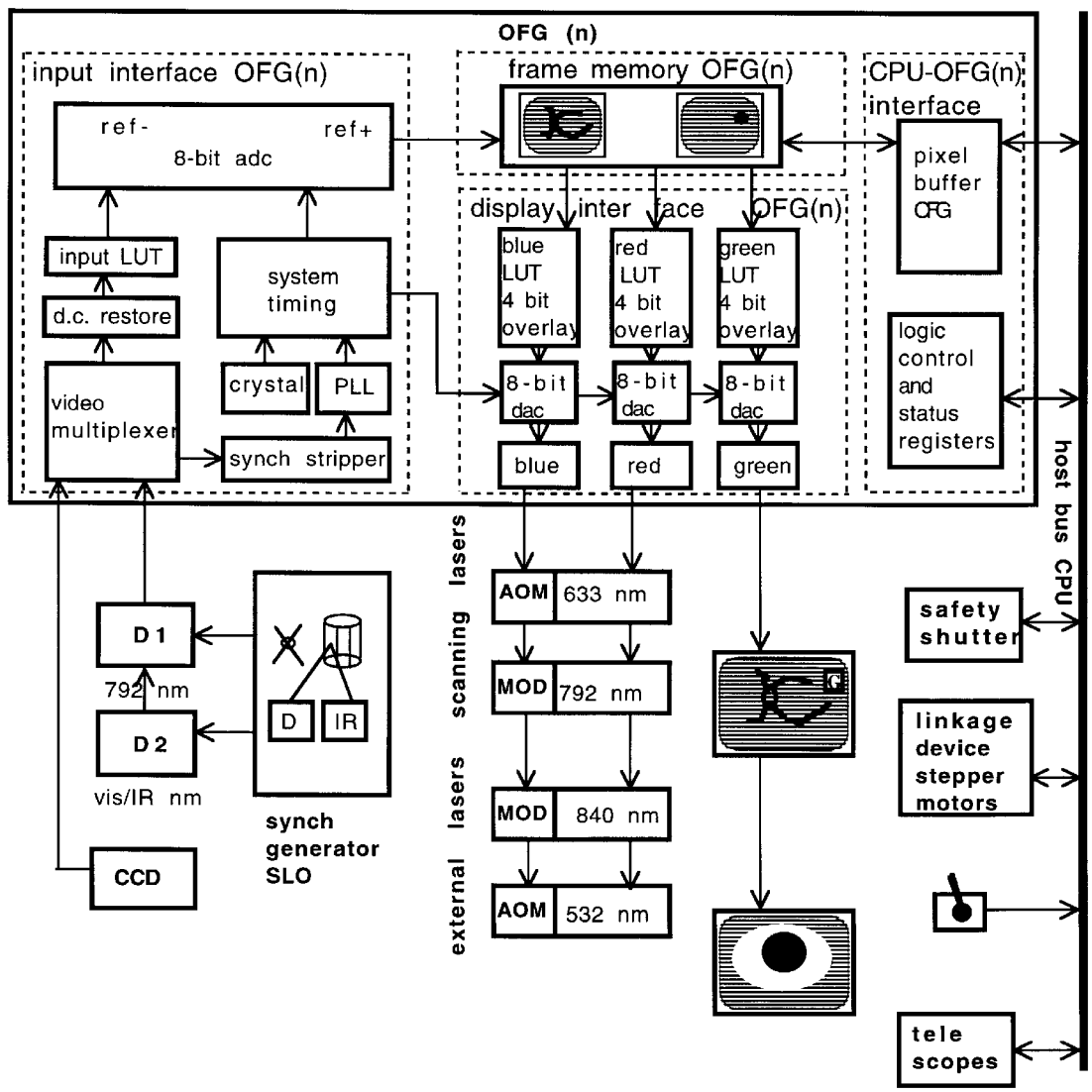
FIG. 4 shows a block diagram of overlay frame grabber card capable of advanced image processing. The overlay frame grabber graphic card(s) have an input interface, frame memory, display interface and CPU interface. Besides the OFG card(s), the host bus accommodates a I/O for interaction with the control circuitry of the therapeutic laser, opto-mechanical linkage device motors. Essential electronic pathways include: (1) video in pathway from SLO detectors and optional CCD camera. (2) Video-out pathway to monitor and laser modulators. (3) synchronization signal generator and genlocking of the other components including A/D converters, D/A converters, and detectors.

Indispensable for processing the video that is generated by the scanning laser ophthalmoscope laser sources 38, 40 and external laser source 52, 54, and for the production of graphics that will be projected onto the retina, is an overlay frame grabber graphics card 32, schematized in FIG. 4. For our applications we used the Imaging Technology OFG card in a 90 Mhz Pentium PC. This overlay frame grabber graphics card 32 can accept four different video input sources, and digitizes the incoming video signals to eight bits of accuracy, at a rate of 60 fields per second (RS-170). On board frame memory can store two 512 by 480 pixel video frames or one larger 512 by 512 pixel video frame. Two or more overlay frame grabber cards 32, which are I/O mapped, can reside in one computer 34. This versatility is important for the combining of the signals from a multidetector scanning laser ophthalmoscope, e.g. in simultaneous recording of the diagnostic laser beam location on the retina with one detector 28 and the retinal image itself with another detector 28.

The analog-to-digital converter of the frame grabber card 32 has programmable negative and positive reference values for calibrating the white and black video signal levels. A look-up table (LUT) controls the input video and can be used for preprocessing contrast and intensity. This feature is particularly useful in facilitating normalized gray scale correlation, a digital image processing technique further explained.

An additional four bits per pixel control the instantaneous switching between 16 different output look-up tables for each pixel. Three independent output channels are provided for each imaging board. The output channels generate RS-170 video adapted for pseudo-color display. Output LUT programming is a well known solution for creating non-destructive graphic overlays. Non-destructive graphic overlays 46 drawn over the incoming video signal generate the graphics visible in the laser raster of the scanning laser ophthalmoscope and indicate the position on the retina of the external laser beam or graphics on the display monitor. In FIG. 4, the green output video channel sends the retinal image to the monitor 36, overlaid with graphics indicating the external laser beam location. The blue output channel of the original video signal is transformed into pure graphics. It controls the acousto-optic modulator 44 and defines what is visible to the observer in the scanning laser ophthalmoscope. This is typically a reference fixation target or test stimulus. The remaining red output channel can be used for different purposes. One option is the control of acousto-optic modulator 62 to create a pulsating external laser beam 52. Another important feature of the overlay frame grabber card is the capability to synchronize to an external video source using a phase-locked loop. This is important since the timing signals provided by the high speed rotating polygon are slightly irregular.

Digital image processing techniques are used for for tracking of a fiducial landmark in the retinal image as in FIG. 5, for locating the external laser beam on the retina as in FIG. 6, and for locating the entrance location of the laserbeams relative to the anatomical pupil of the eye. The overlay frame grabber card 32 can perform this task using for example a technique called two-dimensional normalized gray-scale correlation. Such software is provided by Imaging Technology, Inc, Bedford, Mass. In two-dimensional normalized gray-scale correlation a characteristic search pattern, such as the branching of retinal vessels or the bright patch of light reflected from the external laser beam location is located within the video images provided by the detectors 28 of the scanning laser ophthalmoscope. Sub-pixel accuracy is possible and sometimes necessary for the determination of small displacements in the presence of wavefront aberrations. For facilitating the tracking of the external laser beam location, the reference image in frame memory contains no retinal details as in FIG. 5, for facilitating the tracking of a fiducial landmark on the retina, the fundus image in frame memory is devoid of the therapeutic laser light as in FIG. 6.

In order to reconstruct the wavefront aberrations of the eye optics from reflectometric data, it is necessary to know each entrance position of the diagnostic external beam 52 in relation the the anatomical pupil and furthermore at the same time the distance between the location of the beam on the retinal image and a fixed fiducial retinal landmark. Hence the necessity to retrieve the position of the fiducial landmark on the retina. As mentioned, the distribution of the locations of the external laser on the retina for the various significant entrance positions can then be used to reconstruct the wavefront aberrations over the anatomical pupil using for example well-known Zernike polynomial analysis. One important innovative feature of this reflectonetric technique here is the use of a real retinal image to retrieve a fiducial landmark. If a psychophysical method is used whereby the subject is asked to align with the help of the joystick-micromanipulator 78 the spot of the external laser with the reference fixation target of the scanning laser ophthalmoscope, only the entrance location of the beam in the anatomical pupil needs to be determined.

Although the description of the invention contains many specifications, these should not be construed as limiting the scope of the invention but as merely providing an illustration of the presently preferred embodiment of this invention. Other embodiments of the invention including additions, subtractions, deletions, or modifications of the disclosed embodiment will be obvious to those skilled in the art and are within the scope of the following claims. The scope of the invention should be determined by the appended claims and their legal equivalents, rather than by the example given.

I claim:

1. A combination of a scanning laser ophthalmoscope and external diagnostic laser source, for delivering a diagnostic laser beam of said laser source to the retina of an eye, to determine the wavefront aberrations of the optics of said eye, comprising the elements of:

A. said scanning laser ophthalmoscope, having laser beam of a first wavelength that is scanned through a pivot point, and first detector means for obtaining a video image of said retina of said eye;

B. reference laser beam of a second wavelength within said scanning laser ophthalmoscope, with modulating means to create a reference spot on said retina;

C. said external diagnostic laser source, comprising said diagnostic laser beam of a third wavelength, said diagnostic laser beam producing a diagnostic spot on said retina, further including a means to focus said diagnostic laser beam, and electronical means for controlling the size, duration and intensity of said diagnostic laser beam on the retina;

D. means for optically coupling said scanning laser ophthalmoscope with said diagnostic laser source including a beam splitter on which a coating is applied to permit said laser beam of said first wavelength, said reference laser beam of second wavelength and said diagnostic laser beam of third wavelength to be combined before entering the eye;

E. second detecting means in said scanning laser ophthalmoscope comprising second detector and optical means for detecting by preference said third wavelength, said second detecting means generating a video image that is synchronized with a video image produced by said first detector of said scanning laser ophthalmoscope;

F. means for stabilizing the position of said eye relative to said scanning laser ophthalmoscope;

G. opto-mechanical means for coupling said scanning laser ophthalmoscope with said diagnostic laser source, including a succession of optical interfaces and structural support means joined together to move said diagnostic laser beam in such manner that a multitude of entrance locations is created for said diagnostic laser beam;

H. digital image processing means, comprising of a computer with a frame grabber card capable of generating overlay graphics, said frame grabber card further including means for synchronizing the video images produced by said first and said second detector to timing signals provided by said scanning laser ophthalmoscope, and output means capable of documenting the location of said diagnostic laser beam and said reference laser beam on the retina;

whereby said diagnostic spot and said reference spot are documented on said retina for each said entrance location to derive the wavefront aberrations of the eye optics.

2. The scanning laser ophthalmoscope for the derivation of the wavefront aberrations of the eye optics according to claim 1, further comprising the improvement of having mechanical means to angulate said external diagnostic laser beam for each said entrance location, to superimpose said diagnostic spot with said reference spot on said retina for each said entrance location.

3. The scanning laser ophthalmoscope for the derivation of the wavefront aberrations of the eye optics according to claim 1, further comprising the improvement of having means for visualizing the anterior segment of the eye thereby allowing the registration of said entrance location of said external diagnostic laser beam in the presence of eye movements.

4. The scanning laser ophthalmoscope for the derivation of the wavefront aberrations of the eye optics according to claim 1, using a multiple element solid state laser to create said multitude of entrance locations for said diagnostic laser beam into said eye.

\* \* \* \* \*